United States Patent [19]

Maillefer

[11] Patent Number: 4,871,313
[45] Date of Patent: Oct. 3, 1989

[54] DENTAL PIN

[75] Inventor: Pierre-Luc Maillefer, Canton of Vaud, Switzerland

[73] Assignee: Les Fils d'Auguste Maillefer, Societe Anonyme a Ballaigues, Switzerland

[21] Appl. No.: 238,745

[22] Filed: Aug. 31, 1988

[30] Foreign Application Priority Data

Sep. 8, 1987 [CH] Switzerland .......................... 3464/87

[51] Int. Cl.⁴ ............................................... A61C 5/04
[52] U.S. Cl. ................................................... 433/225
[58] Field of Search ................ 433/225, 221, 173, 174

[56] References Cited

U.S. PATENT DOCUMENTS 4,406,623  9/1983  Grafelmann et al. ............... 433/174
4,759,714  7/1988  Szequary ............................. 433/221

Primary Examiner—Robert Peshock
Attorney, Agent, or Firm—Silverman, Cass & Singer, Ltd.

[57] ABSTRACT

The stem is tubular, being provided with an axial bore and is frusto-conical. It is provided with an outer thread as well as with a helical groove which provides therefor a resiliency enabling its section to adapt itself perfectly to the section of the root canal in which the pin is screwed.

6 Claims, 1 Drawing Sheet

DENTAL PIN

BACKGROUND OF THE INVENTION

The present invention is concerned with a dental pin of the type comprising a stem provided with a head.

The head of the pin serves for the reconstitution, in a composite material or an amalgam, of a stump intended to receive a dental crown, while the stem of the pin is intended to be inserted and sealed in a hole provided in the root of the natural tooth.

SUMMARY OF THE INVENTION

The object of the present invention is to improve the retention of the stem in the hole provided in the root.

This object is achieved in accordance with the invention due to the fact that at least the apical part of the stem is tubular, and is provided with at least one outer thread and one helical groove.

The various features of the invention will be apparent from the following description, drawings and claims the scope of the invention not being limited to the drawings themselves as the drawings are only for the purpose of illustrating ways in which the principles of the invention can be applied. Other embodiments of the invention utilising the sam or equivalent principles may be used and structural changes may be made as desired by those skilled in the art without departing from the present invention and the purview of the appended claims.

DESCRIPTION OF THE PREFERRED EMBODIMENTS

Figure 1:
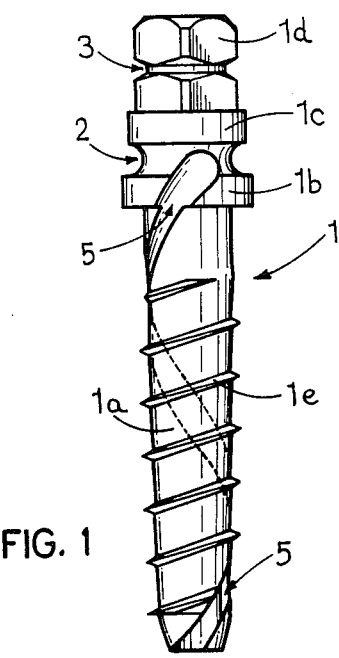
FIG. 1 is an elevational view of a dental pin in accordance with the invention.
Figure 2:
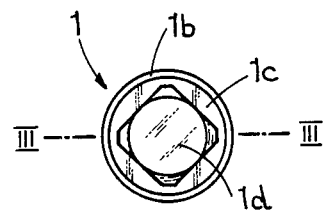
FIG. 2 is a plan view, from above, of the illustrated pin.

The dental pin illustrated, generally designated by the reference 1, comprises a stem 1a, which is frusto-conical, which is prolongated by a head presenting two flanges 1b and 1c, separated from each other by a groove 2, and with a part of square cross-section 1d which is also provided with a groove, designated by the reference 3.

Figure 3:
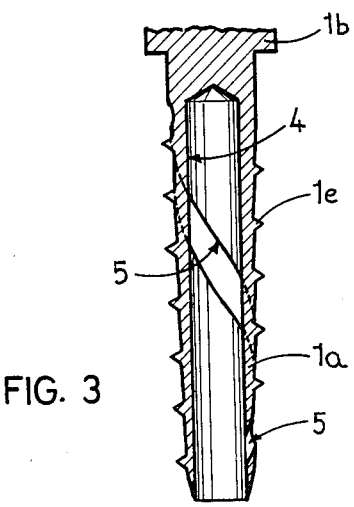
FIG. 3 is a sectional view on the line III—III of FIG. 2 with the head of the pin, except its base, omitted.

The frusto-conical stem 1a is tubular, being provided with a blind axial bore 4, as shown particularly in FIG. 3. It is provided with an outer thread 1e enabling the pin to be screwed into the root canal of the tooth to be reconstituted, after endodontic preparation of this canal, by means of a key engaged on the head 1d. The stem 1a could alternatively be provided with two threads in lieu of the single thread illustrated.

The stem 1a is provided with a helical groove 5, extending up to the level of the groove 2 of the head of the pin and the width of which is substantially constant. This width could however be variable, increasing from the end of the pin in the direction of the head thereof. As a modification, the pin could be provided with two or more helical groove which, in this case, would be narrower than the groove of the pin as described and illustrated.

It is to be noted that the sense of the helix constituted by the helical groove 5, which is in the left hand sense, is the reverse of the sense of the thread 1e, which is a righthand thread.

As a modification, the stem of the pin could be other than frusto-conical in shape, for example cylindrical, or present a cervical part, that is to say the part which is near the crown, which might be cylindrical and followed by an apical part, that is to say the part nearer the point of the root, which might be frusto-conical.

The present arrangement has the advantage that the helical groove gives to the tubular part of the stem of the pin a resiliency which allows its section to adapt itself perfectly to the section of the hole provided in the root of the tooth in which it is screwed.

I claim:

1. A dental pin comprising a stem provided with a head, in which at least an apical part of said stem is tubular, and is provided with at least one outer thread and one helical groove.

2. A dental pin as claimed in claim 1, in which the sense of the heli of the helical groove is the reverse of that of the helix of the thread.

3. A dental pin as claimed in claim 2, in which said helical groove extends beyond the stem of the pin and bites into the head of the pin.

4. A dental pin as claimed in claim 1, in which said helical groove is of constant width throughout its length.

5. A dental pin as claimed in claim 1, in which said helical groove is of variable width, increasing from its terminal part, at the apical end of the pin, in the direction of the head of the pin.

6. A dental pin as claimed in claim 1, in which the stem is tubular and frusto-conical over practically the whole length thereof, up to the immediate vicinity of said head.

* * * * *